United States Patent [19]

Holmwood et al.

[11] 4,262,000
[45] Apr. 14, 1981

[54] COMBATING FUNGI WITH 3-SUBSTITUTED PYRIDINE DERIVATIVES

[75] Inventors: Graham Holmwood, Wuppertal; Paul-Ernst Frohberger, Leverkusen, both of Fed. Rep. of Germany

[73] Assignee: Bayer Aktiengesellschaft, Leverkusen, Fed. Rep. of Germany

[21] Appl. No.: 121,864

[22] Filed: Feb. 15, 1980

[30] Foreign Application Priority Data

Mar. 9, 1979 [DE] Fed. Rep. of Germany ....... 2909287

[51] Int. Cl.³ .................... C07D 213/50; A61K 31/44
[52] U.S. Cl. .................................. 424/263; 546/339; 546/342
[58] Field of Search ................ 546/342, 339; 424/263

[56] References Cited

U.S. PATENT DOCUMENTS 3,320,269  5/1967  De Wald et al. .................... 546/339

Primary Examiner—Alan L. Rotman
Attorney, Agent, or Firm—Sprung, Felfe, Horn, Lynch & Kramer

[57] ABSTRACT

3-Substituted pyridine derivatives of the formula

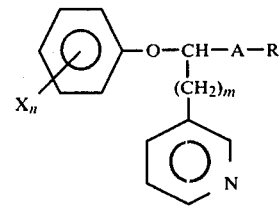

in which
A is —CO— or —CH(OH)—,
R is alkyl or optionally substituted phenyl,
X each independently is halogen, alkyl, cycloalkyl, alkoxy, alkylthio, halogenoalkyl, optionally substituted phenyl, optionally substituted phenoxy, optionally substituted phenylalkyl or optionally substituted phenylalkoxy,
n is 0, 1, 2 or 3, and
m is 0 or 1, or a physiologically acceptable acid addition salt or metal salt complex thereof, which possess fungicidal activity.

10 Claims, No Drawings

COMBATING FUNGI WITH 3-SUBSTITUTED PYRIDINE DERIVATIVES

The present invention relates to certain new 3-substituted pyridine derivatives, to a process for their preparation and to their use as fungicides.

It has already been disclosed that zinc ethylene-1,2-bisdithiocarbamidate is a good agent for combating fungal plant diseases (see Phytopathology 33, 1,113 (1963)). However, it can be used only to a limited extent since it does not always display a completely satisfactory action when low amounts and concentrations are applied.

The present invention now provides, as new compounds, the 3-substituted pyridine derivatives of the general formula

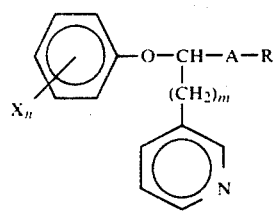

in which
A represents the —CO— or the —CH(OH)— group,
R represents alkyl or optionally substituted phenyl,
X represents halogen, alkyl, cycloalkyl, alkoxy, alkylthio, halogenoalkyl, optionally substituted phenyl, optionally substituted phenoxy, optionally substituted phenylalkyl or optionally substituted phenylalkoxy,
n represents 0, 1, 2 or 3, the X substituents being selected independently of one another when n is 2 or 3, and
m represents 0 or 1,
and physiologically acceptable acid addition salts and metal salt complexes thereof.

The 3-substituted pyridine derivatives of the formula (I) have good fungicidal properties.

Surprisingly, the 3-substituted pyridine derivatives of the formula (I) exhibit a considerably more powerful fungicidal activity, especially against powdery mildew species, than zinc ethylene-1,2-bisdithiocarbamidate, which is known from the state of the art and is a known substance of the same type of action. The active compounds according to the invention thus represent an enrichment of the art.

The preferred 3-substituted pyridine derivatives of the formula (I) are those in which
R represents alkyl with 1 to 4 carbon atoms or optionally substituted phenyl, the substituent or substituents being selected from halogen, alkyl with 1 to 4 carbon atoms and alkoxy with 1 to 2 carbon atoms,
X represents halogen; alkyl, alkoxy or alkylthio with in each case 1 to 4 carbon atoms; cycloalkyl with 5 to 7 carbon atoms; halogenoalkyl with up to 2 carbon atoms and up to 5 identical or different halogen atoms (especially fluorine and chlorine atoms); or phenyl, phenoxy, phenylalkyl with 1 to 2 carbon atoms in the alkyl part or phenylalkoxy with 1 to 2 carbon atoms in the alkyl part, in each case optionally substituted by halogen or alkyl with 1 to 2 carbon atoms; and
n represents 0, 1 or 2.

The compounds of the formula (I) possess an asymmetric carbon atom; they can therefore exist in the form of the two optical isomers or as racemates. All the isomers are comprehended by formula (I).

The invention also provides a process for the preparation of a 3-substituted pyridine derivative of the formula (I) in which
(a) a halogeno-pyridine-ketone of the general formula

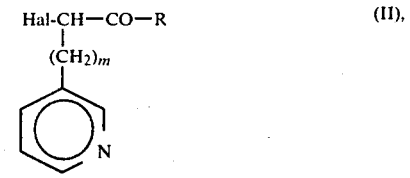

in which
R and m have the meanings indicated above and
Hal represents halogen, preferably chlorine or bromine,
is reacted with a phenol of the general formula

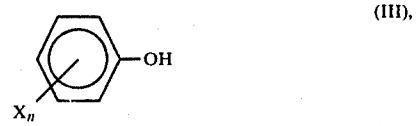

in which
X and n have the meanings indicated above, in the presence of a diluent and in the presence of an acid-binding agent, or
(b) an α,β-unsaturated ketone of the general formula

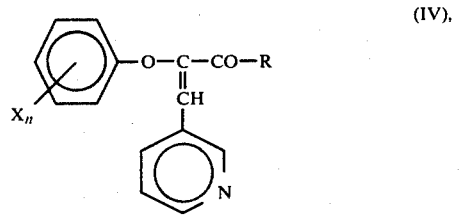

in which
R, X and n have the meanings indicated above, is reacted, in a manner which is in itself known, (α) with hydrogen in the presence of a catalyst and if appropriate in the presence of a polar diluent or (β) with a metal/acid mixture, especially zinc/glacial acetic acid,
(c) the keto derivative of the formula (I) obtainable by process variant (a) or (b) is optionally reduced to the secondary alcohol of the formula (I) by a known method in the customary manner.

An acid or a metal salt can optionally be added onto the compound of the formula (I) obtained in process variant (a), (b) or (c).

Particularly preferred compounds of the formula (I) are those in which R represents tert.-butyl, isopropyl, phenyl, chlorophenyl, fluorophenyl or dichlorophenyl; X represents fluorine, chlorine, bromine, methyl, ethyl, methoxy, methylthio, trifluoromethyl, cyclohexyl, phenyl, chlorophenyl, phenoxy, chlorophenoxy, chlorobenzyl or chlorobenzyloxy; and n represents 0, 1 or 2. In the preferred and the particularly preferred compounds A and the index m have the meanings indicated in the definition of the invention.

The following compounds of the general formula (I) may be mentioned specifically, in addition to the compounds mentioned later in the preparative examples:

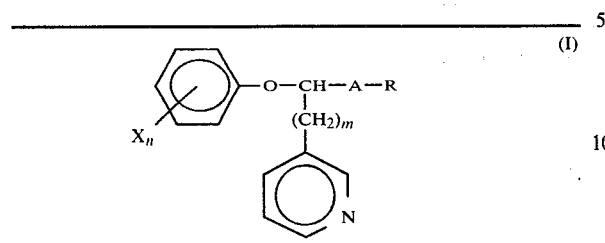
(I)

| $X_n$ | A | R | m |
|---|---|---|---|
| — | CO | C(CH₃)₃ | 0 |
| 4-OCH₃ | CO | C(CH₃)₃ | 0 |
| 4-F | CO | C(CH₃)₃ | 0 |
| 4-CH₃ | CO | C(CH₃)₃ | 0 |
| 3,4-Cl₂ | CO | C(CH₃)₃ | 0 |
| 2-C₂H₅ | CO | C(CH₃)₃ | 0 |
| 4-C₆H₅ | CO | C(CH₃)₃ | 0 |
| 4-(4-Cl-C₆H₄) | CO | C(CH₃)₃ | 0 |
| 4-O-C₆H₅ | CO | C(CH₃)₃ | 0 |
| 4-O-(4-Cl-C₆H₄) | CO | C(CH₃)₃ | 0 |
| 4-cyclohexyl | CO | C(CH₃)₃ | 0 |
| 4-CH₂-(4-Cl-C₆H₄) | CO | C(CH₃)₃ | 0 |
| 4-O-CH₂-(4-Cl-C₆H₄) | CO | C(CH₃)₃ | 0 |
| — | CH(OH) | C(CH₃)₃ | 0 |
| 2,4-Cl₂ | CH(OH) | C(CH₃)₃ | 0 |
| 2-CH₃ | CH(OH) | C(CH₃)₃ | 0 |
| 2-CH₃,4-Cl | CH(OH) | C(CH₃)₃ | 0 |
| 2-Cl | CH(OH) | C(CH₃)₃ | 0 |
| 4-O-CH₃ | CH(OH) | C(CH₃)₃ | 0 |
| 4-F | CH(OH) | C(CH₃)₃ | 0 |
| 4-CH₃ | CH(OH) | C(CH₃)₃ | 0 |
| 3,4-Cl₂ | CH(OH) | C(CH₃)₃ | 0 |
| 2-C₂H₅ | CH(OH) | C(CH₃)₃ | 0 |
| 4-C₆H₅ | CH(OH) | C(CH₃)₃ | 0 |
| 4-(4-Cl-C₆H₄) | CH(OH) | C(CH₃)₃ | 0 |
| 4-O-C₆H₅ | CH(OH) | C(CH₃)₃ | 0 |
| 4-O-(4-Cl-C₆H₄) | CH(OH) | C(CH₃)₃ | 0 |
| 4-cyclohexyl | CH(OH) | C(CH₃)₃ | 0 |
| 4-CH₂-(4-Cl-C₆H₄) | CH(OH) | C(CH₃)₃ | 0 |
| 4-O-CH₂-(4-Cl-C₆H₄) | CH(OH) | C(CH₃)₃ | 0 |
| — | CO | C(CH₃)₃ | 1 |
| 4-OCH₃ | CO | C(CH₃)₃ | 1 |
| 4-F | CO | C(CH₃)₃ | 1 |
| 2-C₂H₅ | CO | C(CH₃)₃ | 1 |
| 4-C₆H₅ | CO | C(CH₃)₃ | 1 |

-continued

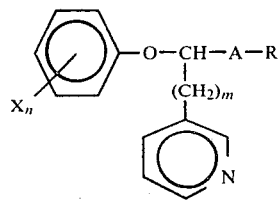
(I)

| $X_n$ | A | R | m |
|---|---|---|---|
| 4-O-C₆H₅ | CO | C(CH₃)₃ | 1 |
| 4-O-(4-Cl-C₆H₄) | CO | C(CH₃)₃ | 1 |
| 4-cyclohexyl | CO | C(CH₃)₃ | 1 |
| 4-CH₂-(4-Cl-C₆H₄) | CO | C(CH₃)₃ | 1 |
| 4-O-CH₂-(4-Cl-C₆H₄) | CO | C(CH₃)₃ | 1 |
| — | CH(OH) | C(CH₃)₃ | 1 |
| 4-Cl | CH(OH) | C(CH₃)₃ | 1 |
| 2,4-Cl₂ | CH(OH) | C(CH₃)₃ | 1 |
| 2-CH₃ | CH(OH) | C(CH₃)₃ | 1 |
| 2-CH₃,4-Cl | CH(OH) | C(CH₃)₃ | 1 |
| 2-Cl | CH(OH) | C(CH₃)₃ | 1 |
| 4-OCH₃ | CH(OH) | C(CH₃)₃ | 1 |
| 4-F | CH(OH) | C(CH₃)₃ | 1 |
| 4-CH₃ | CH(OH) | C(CH₃)₃ | 1 |
| 3,4-Cl₂ | CH(OH) | C(CH₃)₃ | 1 |
| 2-C₂H₅ | CH(OH) | C(CH₃)₃ | 1 |
| 4-C₆H₅ | CH(OH) | C(CH₃)₃ | 1 |
| 4-(4-Cl-C₆H₄) | CH(OH) | C(CH₃)₃ | 1 |
| 4-O-C₆H₅ | CH(OH) | C(CH₃)₃ | 1 |
| 4-O-(4-Cl-C₆H₄) | CH(OH) | C(CH₃)₃ | 1 |
| 4-cyclohexyl | CH(OH) | C(CH₃)₃ | 1 |
| 4-CH₂-(4-Cl-C₆H₄) | CH(OH) | C(CH₃)₃ | 1 |
| 4-O-CH₂-(4-Cl-C₆H₄) | CH(OH) | C(CH₃)₃ | 1 |
| 4-Cl | CO | cyclohexyl | 0 |
| 2,4-Cl₂ | CO | cyclohexyl | 0 |
| 2-CH₃,4-Cl | CO | cyclohexyl | 0 |
| 2-CH₃ | CO | cyclohexyl | 0 |
| 4-Cl | CH(OH) | cyclohexyl | 0 |
| 2,4-Cl₂ | CH(OH) | cyclohexyl | 0 |
| 2-CH₃,4-Cl | CH(OH) | cyclohexyl | 0 |

-continued $$\begin{array}{c} \text{(I)} \\ \underset{X_n}{\phantom{X}}\text{Ar}-\text{O}-\text{CH}-\text{A}-\text{R} \\ |\\ (CH_2)_m\\ \text{Pyridyl} \end{array}$$

| $X_n$ | A | R | m |
|---|---|---|---|
| 2-CH₃ | CH(OH) | phenyl | 0 |
| 4-Cl | CO | phenyl | 1 |
| 2,4-Cl₂ | CO | phenyl | 1 |
| 2-CH₃,4-Cl | CO | phenyl | 1 |
| 2-CH₃ | CO | phenyl | 1 |
| 4-Cl | CH(OH) | phenyl | 1 |
| 2,4-Cl₂ | CH(OH) | phenyl | 1 |
| 2-CH₃,4-Cl | CH(OH) | phenyl | 1 |
| 2-CH₃ | CH(OH) | phenyl | 1 |
| 4-Cl | CO | 4-Cl-phenyl | 0 |
| 2,4-Cl₂ | CO | 4-Cl-phenyl | 0 |
| 2-CH₃,4-Cl | CO | 4-Cl-phenyl | 0 |
| 2-CH₃ | CO | 4-Cl-phenyl | 0 |
| 4-Cl | CH(OH) | 4-Cl-phenyl | 0 |
| 2,4-Cl₂ | CH(OH) | 4-Cl-phenyl | 0 |
| 2-CH₃,4-Cl | CH(OH) | 4-Cl-phenyl | 0 |
| 2-CH₃ | CH(OH) | 4-Cl-phenyl | 0 |
| 4-Cl | CO | 4-Cl-phenyl | 1 |
| 2,4-Cl₂ | CO | 4-Cl-phenyl | 1 |
| 2-CH₃,4-Cl | CO | 4-Cl-phenyl | 1 |
| 2-CH₃ | CO | 4-Cl-phenyl | 1 |
| 4-Cl | CH(OH) | 4-Cl-phenyl | 1 |
| 2,4-Cl₂ | CH(OH) | 4-Cl-phenyl | 1 |
| 2-CH₃,4-Cl | CH(OH) | 4-Cl-phenyl | 1 |
| 2-CH₃ | CH(OH) | 4-Cl-phenyl | 1 |
| 4-Cl | CO | 2,4-Cl₂-phenyl | 1 |
| 2,4-Cl₂ | CO | 2,4-Cl₂-phenyl | 1 |
| 2-CH₃,4-Cl | CO | 2,4-Cl₂-phenyl | 1 |
| 2-CH₃ | CO | 2,4-Cl₂-phenyl | 1 |
| 4-Cl | CH(OH) | 2,4-Cl₂-phenyl | 0 |
| 2,4-Cl₂ | CH(OH) | 2,4-Cl₂-phenyl | 0 |
| 2-CH₃,4-Cl | CH(OH) | 2,4-Cl₂-phenyl | 0 |
| 2-CH₃ | CH(OH) | 2,4-Cl₂-phenyl | 0 |
| 4-Cl | CO | 2,4-Cl₂-phenyl | 1 |
| 2,4-Cl₂ | CO | 2,4-Cl₂-phenyl | 1 |
| 2-CH₃,4-Cl | CO | 2,4-Cl₂-phenyl | 1 |
| 2-CH₃ | CO | 2,4-Cl₂-phenyl | 1 |
| 4-Cl | CH(OH) | 2,4-Cl₂-phenyl | 1 |
| 2,4-Cl₂ | CH(OH) | 2,4-Cl₂-phenyl | 1 |
| 2-CH₃,4-Cl | CH(OH) | 2,4-Cl₂-phenyl | 1 |

-continued

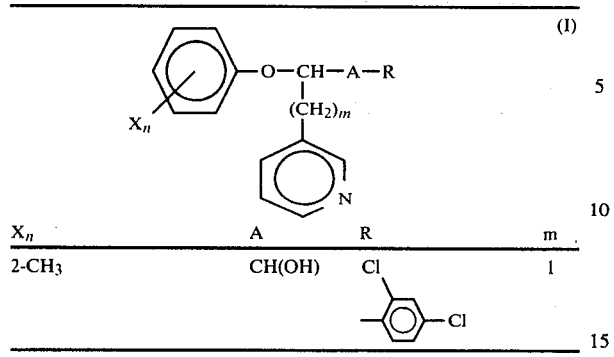

| $X_n$ | A | R | m |
|---|---|---|---|
| 2-CH$_3$ | CH(OH) | Cl—⌬—Cl | 1 |

If, for example, 1-bromo-3,3-dimethyl-1-pyridin-3-yl-butan-2-one and 4-chlorophenol are used as starting materials in process variant (a), the course of the reaction can be represented by the following equation:

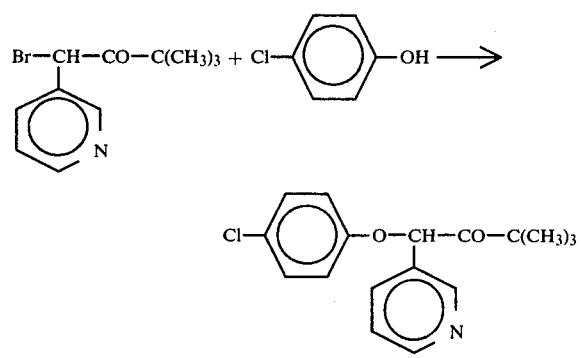

If, for example, 2-(4-chlorophenoxy)-4,4-dimethyl-1-pyridin-3-yl-1-penten-3-one and a mixture of zinc/acetic acid are used as starting materials in process variant (b), the course of the reaction can be represented by the following equation:

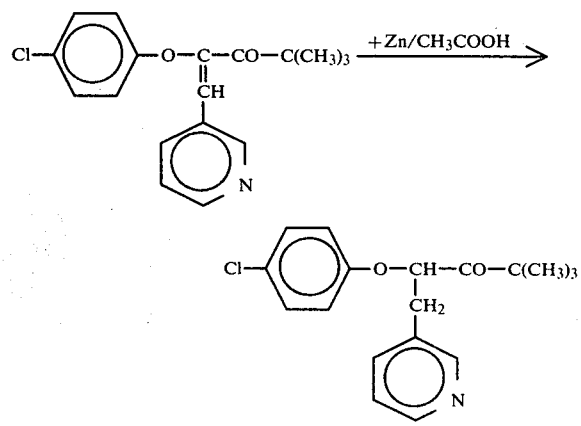

If, for example, 1-(4-chlorophenoxy)-3,3-dimethyl-1-pyridin-3-yl-butan-2-one and sodium borohydride are used as starting materials in process variant (c), the course of the reaction can be represented by the following equation:

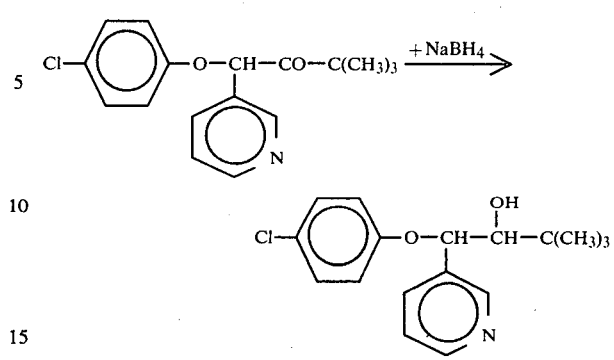

The formula (II) provides a general definition of the halogeno-pyridine-ketones to be used as starting substances in process variant (a). In this formula, R preferably represents those radicals which have already been mentioned as preferred in the description of the substances of the formula (I) and m is 0 or 1.

The halogeno-pyridine-ketones of the formula (II) have not hitherto been described in the literature, but they can be prepared by known processes, by replacing one of the two active hydrogen atoms in pyridine-ketones of the general formula

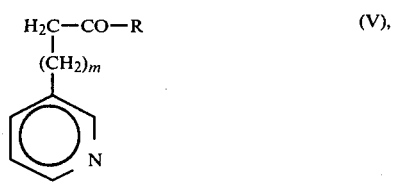

in which R and m have the meanings indicated above, by halogen in the customary manner (see also the preparative examples).

Pyridine-ketones of the formula (V) in which m represents 0 are known, for example from Synthesis 1975, 705, and they can easily be prepared by the processes described in this reference, for example by reacting corresponding carboxylic acid esters with the lithium derivative of 2-picoline. The pyridine-ketones of the formula (V) in which m represents 0 can also be obtained by reacting 3-pyridylacetic acid ethyl ester or 3-pyridylacetic acid nitrile with Grignard compounds of the R-Mg-Hal type in a generally known manner, the latter compounds being obtained from the corresponding halides R-Hal and magnesium in the customary manner.

Pyridine-ketones of the formula (V) in which m represents 1 are likewise known, for example from Arch. Pharm. 1974, 307, 550, and they can easily be prepared by the processes described in this reference, by reacting the corresponding ketone of the general formula $$H_3C-CO-R \qquad (VI).$$

in which R has the meaning indicated above, with 3-pyridinealdehydes and reducing the resulting product of the formula

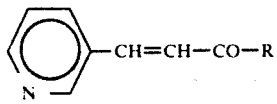 (VII), in which R has the meaning indicated above, with hydrogen in the presence of a catalyst, preferably Raney nickel (see also the preparative examples).

Examples of the halogeno-pyridine-ketones of the formula (II) which may be mentioned are:

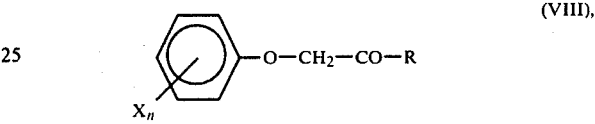

| R | m | R | m |
|---|---|---|---|
| C(CH₃)₃ | 0 | C(CH₃)₃ | 1 |
| i-C₃H₇ | 0 | i-C₃H₇ | 1 |
| phenyl | 0 | phenyl | 1 |
| 4-Cl-phenyl | 0 | 4-Cl-phenyl | 1 |
| 4-F-phenyl | 0 | 4-F-phenyl | 1 |
| 4-Br-phenyl | 0 | 4-Br-phenyl | 1 |
| 2,4-Cl₂-phenyl | 0 | 2,4-Cl₂-phenyl | 1 |
| 3,4-Cl₂-phenyl | 0 | 3,4-Cl₂-phenyl | 1 |
| 4-CH₃-phenyl | 0 | 4-CH₃-phenyl | 1 |
| 4-C₂H₅-phenyl | 0 | 4-C₂H₅-phenyl | 1 |
| 3-CH₃-4-Cl-phenyl | 0 | 3-CH₃-4-Cl-phenyl | 1 |
| 4-OCH₃-phenyl | 0 | 4-OCH₃-phenyl | 1 |
| 3,4-Cl₂-phenyl | 0 | 3,4-Cl₂-phenyl | 1 |
| 2,4-Cl₂-phenyl | 0 | 2,4-Cl₂-phenyl | 1 |
| 4-CH₃-phenyl | 0 | 4-CH₃-phenyl | 1 |

The formula (III) provides a general definition of the phenols also to be used as starting substances in process variant (a). In this formula, X and n preferably have those meanings which have already been mentioned as preferred in the description of the substances of the formula (I).

The phenols of the formula (III) are generally known compounds of organic chemistry. Examples which may be mentioned are: phenol, 4-chlorophenol, 4-fluorophenol, 4-methylphenol, 4-methoxyphenol, 2-chlorophenol, 2-methylphenol, 2-ethylphenol, 4-phenylphenol, 4-phenoxyphenol, 4-4'-chlorophenylphenol, 4-4'-chlorophenoxyphenol, 2,4-dichlorophenol, 3,4-dichlorophenol, 2,6-dichlorophenol and 2-methyl-4-chlorophenol.

The formula (IV) provides a general definition of the α,β-unsaturated ketones to be used as starting substances in process variant (b). In this formula, R, X and n preferably have those meanings which have already been mentioned as preferred in the description of the substances of the formula (I).

The α,β-unsaturated ketones of the formula (IV) are interesting new intermediate products. They are obtained when phenoxyketones of the general formula

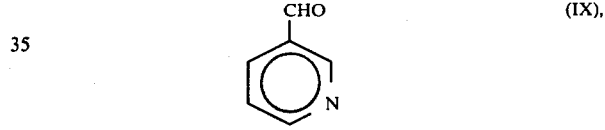 (VIII), in which R, X and n have the meanings indicated above, are reacted with 3-pyridinealdehydes of the general formula $$\underset{N}{\underset{\|}{\bigcirc}}\text{—CHO}$$ (IX), in the presence of a diluent and in the presence of a base.

Phenoxyketones of the formula (VIII) are known compounds (in this context, see DE-OS (German Published Specification) No. 2,105,490 (Le A 13 458) and U.S. Pat. No. 3,812,142, and DE-OS (German Published Specification) No. 2,201,063 (Le A 14 118) and U.S. Pat. No. 3,912,752), and they can easily be prepared by processes which have been described (so-called Williamson ether synthesis).

Regarding the preparation of the new intermediate products of the formula (IV), preferred diluents for the reaction of the phenoxy-ketones of the formula (VIII) with the 3-pyridinealdehyde of the formula (IX) are water and inert organic solvents. These include, as preferences, ethers, such as diethyl ether or tetrahydrofuran; alcohols, such as methanol or ethanol; and dimethylsulphoxide and dimethylformamide. Mixtures of water with an inert organic solvent are also preferably employed.

Preferred bases are tertiary amines, such as triethylamine; alkali metal carbonates, such as potassium carbonate; alkali metal hydroxides, such as sodium hydroxide; and alkali metal alcoholates, such as sodium methylate.

The reaction temperatures can be varied within a substantial range. In general, the reaction is carried out between −20° and 120° C., preferably between 0° and 80° C.

In carrying out this reaction, 1 to 2 mols of 3-pyridinealdehyde are preferably employed per mol of phenoxyketone of the formula (VIII). The compounds of the formula (IV) are isolated in the customary manner (see also the preparative examples).

Preferred diluents for the reaction in process variant (a) are inert organic solvents. These include, as preferences, ethers, such as diethyl ether; alcohols, such as methanol; ketones, such as acetone; aromatic hydrocarbons, such as benzene; and also dimethylsulphoxide and dimethylformamide.

The reaction in process variant (a) is carried out in the presence of an acid-binding agent. It is possible to add any of the inorganic or organic acid-binding agents which can customarily be used, such as an alkali metal carbonate, for example potassium carbonate or sodium carbonate, an alkali metal hydroxide, for example sodium hydroxide, an alkali metal alcoholate, for example sodium methylate, or a lower tertiary alkylamine, for example triethylamine.

The reaction temperatures can be varied within a substantial range in carrying out process variant (a). In general, the reaction is carried out at from 0° to 140° C., preferably from 50° to 100° C.

In carrying out process variant (a), 2 to 4 mols of phenol of the formula (III) are preferably employed per mol of the compound of the formula (II). The resultant compound of the formula (I) is isolated in the customary manner. The compounds of the formula (II) are preferably employed in the form of their hydrohalides.

Possible diluents for the reaction in process variant (b)($\alpha$) are polar organic solvents. These include, as preferences, alcohols, such as methanol and ethanol, and nitriles, such as acetonitrile.

The reaction in process variant (b)($\alpha$) is carried out in the presence of a catalyst. The catalysts preferably used are noble metal, noble metal oxide or noble metal hydroxide catalysts or so-called Raney catalysts, especially platinum, platinum oxide or nickel.

The reaction temperatures can be varied within a substantial range in carrying out process variant (b)($\alpha$). In general, the reaction is carried out at from 0° to 50° C., preferably from 20° to 40° C.

The reaction in process variant (b)($\alpha$) can be carried out not only under normal pressure, but also under increased pressure, such as 1 to 2 atmospheres gauge.

In carrying out process variant (b)($\alpha$), about 1 mol of hydrogen and 0.1 mol of catalyst are preferably employed per mol of the compound of the formula (IV). To isolate the resultant compound of the formula (I), the catalyst is filtered off, the filtrate is freed from solvent in vacuo and the resulting product is purified in the customary manner.

The reaction temperatures can be varied within a substantial range in carrying out process (b)($\beta$). In general, the reaction is carried out at from 50° to 150° C., preferably from 80° to 120° C.

In carrying out process variant (b)($\beta$), 3 to 4 mols of metal are preferably employed per mol of the compound of the formula (IV). The resultant compound of the formula (I) is isolated in the customary manner.

Process variant (c), that is the reduction of the keto compounds of the formula (I) to give the corresponding secondary alcohols, is carried out in the customary manner, for example by reaction with complex hydrides, if appropriate in the presence of a diluent, or by reaction with aluminum isopropylate in the presence of a diluent.

If complex hydrides are used, possible diluents for the reaction are polar organic solvents. These include, as preferences, alcohols, such as methanol, ethanol, butanol or isopropanol, and ethers, such as diethyl ether or tetrahydrofuran. The reaction is in general carried out at from 0° to 30° C., preferably at from 0° to 20° C. About 1 mol of a complex hydride, such as sodium borohydride or lithium alanate, is generally employed per mol of the ketone of the formula (I). To isolate the reduced compound of the formula (I), the residue is taken up in dilute hydrochloric acid and the mixture is then rendered alkaline and extracted with an organic solvent. Further working up is effected in the customary manner.

If aluminum isopropylate is used, preferred diluents for the reaction are alcohols, such as isopropanol, or inert hydrocarbons, such as benzene. The reaction temperatures can again be varied within a substantial range; in general, the reaction is carried out at from 20° to 120° C., preferably at from 50° to 100° C. For carrying out the reaction, about 1 to 2 mols of aluminum isopropylate are employed per mol of the ketone of the formula (I). To isolate the reduced compounds of the formula (I), excess solvent is removed by distillation in vacuo and the aluminum compound formed is decomposed with dilute sulphuric acid or sodium hydroxide solution. Further working up is effected in the customary manner.

Any of the physiologically acceptable acids can be used for the preparation of acid addition salts of the compounds of the formula (I). These acids include, as preferences, hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiologically acceptable acids. These include, as preferences, hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteronycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating powdery mildew fungi, such as for combating powdery mildew of cereals; in addition they can be used against the apple scab causative organism (*Fusicladium dendriticum*), and for combating the fungi Pyricularia and Pellicularia.

Furthermore, the new intermediate products of the formula (IV) also exhibit a fungicidal action.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimetylsulphoxide, as ell as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphtes, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of, in general, 0.001 to 50 g, preferably 0.01 to 10 g, are generally employed per kilogram of seed.

For the treatment of soil, active compound concentrations of, in general, 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

Process variant (a)

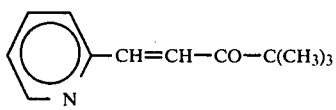
(a)

100 ml of 10% strength sodium hydroxide solution were added to a solution of 35 g (0.35 mol) of 3,3-dimethylbutan-2-one and 38 g (0.355 mol) of 3-pyridinealdehyde in 2,000 ml of water and the solution was stirred overnight at room temperature. The crystalline precipitate was filtered off, dried and recrystallized from n-hexane. 34.1 g (51.5% of theory) of 4,4-dimethyl-1-pyridin-3-yl-1-penten-3-one of melting point 68°–70° C. were obtained.

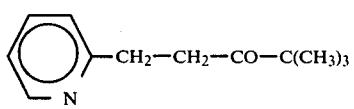
(b)

154.2 g (0.814 mol) of 4,4-dimethyl-1-pyridin-3-yl-1-penten-3-one were dissolved in 750 ml of tetrahydrofuran and the solution was stirred with about 20 g of Raney nickel. The solution was filtered, a further 20 g of Raney nickel were added and hydrogenation was carried out under the usual pressure and at room temperature until, according to the thin layer chromatogram, no further starting material was present. The Raney nickel was filtered off from the solution, the filtrate was concentrated and the residue was distilled. 119.8 g (78% of theory) Of 4,4-dimethyl-1-pyridin-3-yl-pentan-3-one of boiling point 123°–130° C./2.3 mm Hg were obtained.

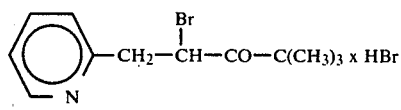
(c)

320.5 g (1.676 mol) of 4,4-dimethyl-1-pyridin-3-yl-pentan-3-one were dissolved in 320 ml of aqueous 48% strength hydrobromic acid, and 267.8 g (85.3 ml; 1.65 mol) of bromine were added dropwise at 80° to 95° C. in the course of 2 hours. When the addition had ended, the solution was cooled and concentrated. The solid which remained was comminuted well, stirred with about 1.5 liters of ethanol, filtered off, washed with ethanol and dried. 450 g (78% of theory) of 2-bromo-4,4-dimethyl-1-pyridin-3-yl-pentan-3-one of melting point 163°–64° C. were obtained.

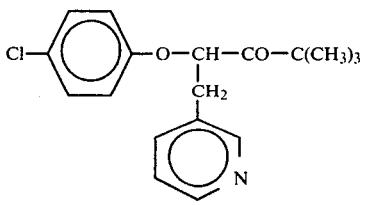
(d)

38.6 g (0.3 mol) Of 4-chlorophenol were dissolved in 200 ml of absolute methanol, and 6.9 g (0.3 mol) of sodium were added. When the sodium had dissolved completely, the solution was heated under reflux for 30 minutes and 35.1 g (0.1 mol) of 2-bromo-4,4-dimethyl-1-pyridin-3-yl-pentan-3-one hydrobromide were added all at once, whilst the mixture simmered. The reaction mixture was heated under reflux overnight and, after cooling, was concentrated. The residue was taken up in ether and 2 N sodium hydroxide solution and the ether phase was separated off, washed twice with 2 N sodium hydroxide solution, once with water and once with saturated sodium chloride solution and then dried over sodium sulphate and concentrated. After recrystallization of the residue from cyclohexane, 3.3 g (11.5% of theory) of 2-(4-chlorophenoxy)-4,4-dimethyl-1-pyridin-3-yl-pentan-3-one of melting point 76°–78° C. were obtained.

EXAMPLE 2

Process variant (b)

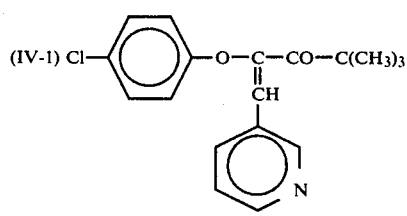
(IV-1) (a)

100 ml of water, followed by 28 ml of 10% strength aqueous sodium hydroxide solution, were added to a stirred solution of 22.6 g (0.1 mol) of 1-(4-chlorophenoxy)-3,3-dimethyl-butan-2-one and 21.4 g (0.2 mol) of 3-pyridinealdehyde in 500 ml of methanol. The solution was subsequently stirred at room temperature for 4 days, the methanol was removed in vacuo and the aqueous residue was taken up in ether. The aqueous phase was separated off, the organic phase was extracted three times with 1 N hydrochloric acid and the hydrochloric acid extracts were neutralized with solid sodium bicarbonate and extracted three times with ethyl acetate. 22.8 g (72% of theory) Of 2-(4-chlorophenoxy)-4,4-dimethyl-1-pyridin-3-yl-1-penten-3-one of melting point 74°–76° C. were obtained from the ethyl acetate phase.

The following new intermediate products of the general formula

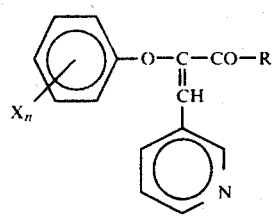

(IV)

were obtained analogously:

| Intermediate No. | $X_n$ | R | Melting point (°C.) |
|---|---|---|---|
| IV-2 | 2-CH₃ | C(CH₃)₃ | 91-93 |
| IV-3 | 2,4-Cl₂ | C(CH₃)₃ | 253-55(x½ NDS) |
| IV-4 | 3,4-Cl₂ | C(CH₃)₃ | 85-86 |
| IV-5 | 4-F | C(CH₃)₃ | 71-73 |
| IV-6 | 4-OCH₃ | C(CH₃)₃ | 87-88 |
| IV-7 | 2-Cl | C(CH₃)₃ | 71-73 |
| IV-8 | 2-CH₃,4-Cl | C(CH₃)₃ | 249-51(x½ NDS) |
| IV-9 | — | C(CH₃)₃ | 46-48 |
| IV-10 | 2,4-Cl₂ | 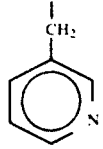 | 117-18 |
| IV-11 | 4-F | 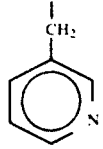 | 98-100 |
| IV-12 | 2-CH₃,4-Cl | 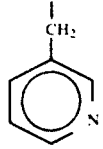 | 118-20 |
| IV-13 | — | 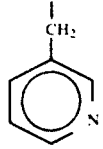 | 112-14 |
| IV-14 | 4-CH₃ | 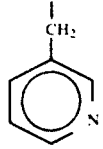 | 80-81,5 |
| IV-15 | 4-OCH₃ | 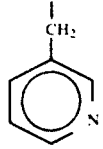 | 96,5-98 |
| IV-16 | 2-CH₃ | 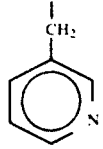 | 132-33 |
| IV-17 | 2-C₂H₅ | 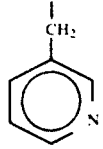 | 62-66 |
| IV-18 | 4-O—CH₂—⟨⟩ | C(CH₃)₃ | 172-75(x½ NDS) |

NDS  1,5-naphthalenedisulphonic acid (b) Cl—⟨⟩—O—CH—CO—C(CH₃)₃  (1)
           |
           CH₂
           |
           ⟨pyridyl⟩

32 g (0.49 mol) of zinc dust were added to 48 g (0.152 mol) of 2-(4-chlorophenoxy)-4,4-dimethyl-1-pyridin-3-yl-1-penten-3-one, dissolved in 170 ml of glacial acetic acid, and the mixture was heated under reflux on an oil bath for 40 minutes. The zinc was filtered off from the solution and rinsed with glacial acetic acid and the acetic acid solution was concentrated. The residue was rendered alkaline with 1 N sodium hydroxide solution and extracted three times with ethyl acetate. From the ethyl acetate phase, 29.9 g (62% of theory) of 2-(4-chlorophenoxy)-4,4-dimethyl-1-pyridin-3-yl-pentan-3-one of melting point 77°-79° C. were obtained after recrystallization from cyclohexane.

EXAMPLE 3

Process variant (a)

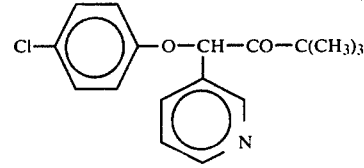

(2)

6.9 g (0.3 mol) of sodium metal were added to a solution of 38.6 g (0.3 mol) of 4-chlorophenol in 200 ml of absolute methanol. When the sodium had dissolved completely, the solution was heated under reflux and 33.7 g (0.1 mol) of 1-bromo-3,3-dimethyl-1-pyridin-3-yl-butan-2-one hydrobromide were added. The reaction mixture was heated under reflux overnight. It was allowed to cool and was concentrated in vacuo. The residue was taken up in diethyl ether and the ether mixture was washed twice with 2 N sodium hydroxide solution, once with water and once with saturated sodium chloride solution, dried over sodium sulphate and concentrated. The residue was recrystallized from n-hexane. 18.8 g (62% of theory) of 1-(4-chlorophenoxy)-3,3-dimethyl-1-pyridin-3-yl-butan-2-one of melting point 50° C. were obtained.

EXAMPLE 4

Reduction; process variant(c)

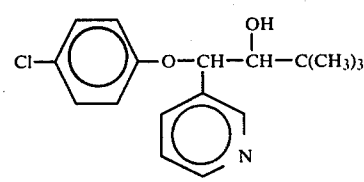

(3)

1.9 g (0.05 mol) of sodium borohydride were added to a solution of 15.2 g (0.05 mol) of 1-(4-chlorophenoxy)-3,3-dimethyl-1-pyridin-3-yl-butan-2-one (Example 3) in 100 ml of absolute ethanol. The reaction mixture was stirred overnight and then water and a little dilute hydrochloric acid were added. The mixture was concentrated by distilling off the ethanol in vacuo. The aqueous residue was rendered alkaline with a saturated sodium bicarbonate solution and extracted three times with ethyl acetate. The combined ethyl acetate phases were dried over sodium sulphate and concentrated. After recrystallizing the residue from cyclohexane, 7.2 g (47% of theory) of 1-(4-chlorophenoxy)-3,3-dimethyl-1-pyridin-3-yl-butan-2-ol of melting point 116°-117° C. were obtained.

The following compounds of the general formula

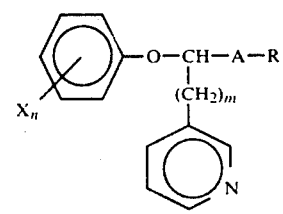

(I)

were obtained in a manner analogous to Example 1 to 3:

| Compound No. | $X_n$ | A | R | m | Melting point (°C.) |
|---|---|---|---|---|---|
| 4 | 2,4-Cl$_2$ | CO | C(CH$_3$)$_3$ | 0 | 74 |
| 5 | 2-CH$_3$ | CO | C(CH$_3$)$_3$ | 0 | 212 (x½NDS) |
| 6 | 2-CH$_3$,4-Cl | CO | C(CH$_3$)$_3$ | 0 | 226–27(x½NDS) |
| 7 | 2-Cl | CO | C(CH$_3$)$_3$ | 0 | 230–31(x½NDS) |
| 8 | 4–⌬–Cl | CO | C(CH$_3$)$_3$ | 0 | 131 |
| 9 | 2,4-Cl$_2$ | CO | ⌬ | 0 | 151–53 |
| 10 | 2-CH$_3$,4-Cl | CO | ⌬ | 0 | 137–38 |
| 11 | 3,4-Cl$_2$ | CO | C(CH$_3$)$_3$ | 1 | 87–88 |
| 12 | 2-CH$_3$ | CO | C(CH$_3$)$_3$ | 1 | 198–200 (x½NDS) |
| 13 | 2,4-Cl$_2$ | CO | C(CH$_3$)$_3$ | 1 | 212–14(x½NDS) |
| 14 | 4–⌬–Cl | CO | C(CH$_3$)$_3$ | 1 | 93–94 |
| 15 | 2-Cl | CO | C(CH$_3$)$_3$ | 1 | 217(x½NDS) |
| 16 | — | CO | C(CH$_3$)$_3$ | 1 | 52–54 |
| 17 | 4-CH$_3$ | CO | C(CH$_3$)$_3$ | 1 | 54–56 |
| 18 | 2-CH$_3$,4-Cl | CO | C(CH$_3$)$_3$ | 1 | 199–201 (x½NDS) |
| 19 | 4-O—CH$_2$–⌬ | CO | C(CH$_3$)$_3$ | 1 | 113–14 |
| 20 | 2,4-Cl$_2$ | CO | C(CH$_3$)$_3$ | 1 | 155–57,5 (x HCl) |

NDS = 1,5-naphthalenedisulphonic acid

The fungicidal activity of the compounds of this invention is illustrated by the following example wherein the compounds of according to the present invention are each identified by the number (given in brackets) from the preparative examples hereinabove:

EXAMPLE 5

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After-drying, the barley plants were dusted with spores of *Erysiphe graminis* var. hordei.

After 6 days' dwell time of the plants at a temperature of 21–22 deg.C and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds showed a very good action which was superior to that of the compounds known from the prior art: (4), (2), (5), (6), (7), (8) and (3).

It will be appreciated that the instant specification and examples are set forth by way of illustration and not limitation, and that various modifications and changes may be made without departing from the spirit and scope of the present invention.

What is claimed is:

1. A 3-substituted pyridine derivative of the formula

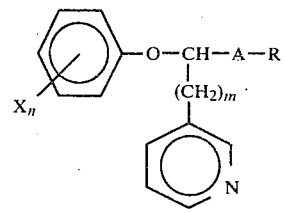

in which

A is —CO— or CH(OH)—,

R is alkyl with 1 to 4 carbon atoms, phenyl or phenyl substituted with halogen, alkyl with 1 to 4 carbon atoms or alkoxy with 1 to 2 carbon atoms, X each independently is halogen; alkyl, alkoxy or alkylthio with in each case 1 to 4 carbon atoms; cycloalkyl with 5 to 7 carbon atoms; halogenoalkyl with up to 2 carbon atoms and up to 5 identical or different halogen atoms; or phenyl, phenoxy, phenylalkyl with 1 to 2 carbon atoms in the alkyl part or phenylalkoxy with 1 to 2 carbon atoms in the alkyl part, in each case optionally substituted by halogen or alkyl with 1 to 2 carbon atoms, n is 0, 1, 2 or 3, and m is 0 or 1, or a physiologically acceptable acid addition salt thereof.

2. A compound according to claim 1 in which n is 0, 1 or 2.

3. A compound according to claim 1 wherein the acid of the acid addition salt is a hydrogen halide acid, phosphoric acid, sulphuric acid, nitric acid, a monofunctional or bifunctional carboxylic or hydroxycarboxylic acid, or a sulphonic acid.

4. A compound according to claim 1, wherein such compound is 1-(4-chloro-phenoxy)-3,3-dimethyl-1-pyridin-3-yl-butan-2-one of the formula

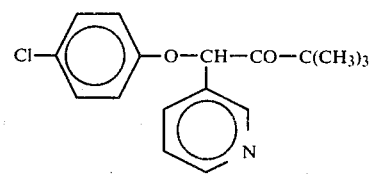

or a physiologically acceptable acid addition salt thereof.

5. A compound according to claim 1, wherein such compound is 1-(4-chloro-phenoxy)-3,3-dimethyl-1-pyridin-3-yl-butan-2-ol of the formula

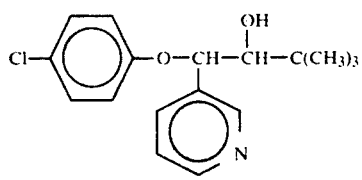

or a physiologically acceptable acid addition salt thereof.

6. A compound according to claim 1 wherein such compound is 1-(2,4-dichlorophenoxy)-3,3-dimethyl-1-pyridin-3-yl-butan-2-one of the formula

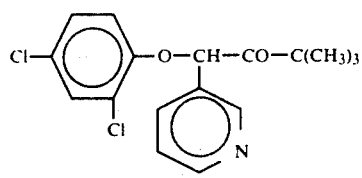

or a physiologically acceptable acid addition salt thereof.

7. A compound according to claim 1, wherein such compound is 1-(2,4-dichlorophenoxy)-3,3-dimethyl-1-(pyridin-3-yl-methyl)-butan-2-one of the formula or a physiologically acceptable acid addition salt thereof.

8. A fungicidal composition containing as active ingredient a fungicidally effective amount of a compound according to claim 1 in admixture with a diluent.

9. A method of combating fungi which comprises applying to the fungi, or to a habitat thereof, a fungicidally effective amount of a compound according to claim 1.

10. The method according to claim 9, in which said compound is
1-(4-chloro-phenoxy)-3,3-dimethyl-1-pyridin-3-yl-butan-2-one,
1-(4-chloro-phenoxy)-3,3-dimethyl-1-pyridin-3-butan-2-ol,
1-(2,4-dichlorophenoxy)-3,3-dimethyl-1-pyridin-3-yl-butan-2-one or
1-(2,4-dichlorophenoxy)-3,3-dimethyl-1-(pyridin-3-yl-methyl)-butan-2-one
or a physiologically acceptable acid addition salt thereof.

* * * * *